United States Patent [19]

Montgomery

[11] 4,418,477
[45] Dec. 6, 1983

[54] MEASURING TAPE

[75] Inventor: John R. Montgomery, Toledo, Ohio

[73] Assignee: Jobst Institute, Inc., Toledo, Ohio

[21] Appl. No.: 264,862

[22] Filed: May 18, 1981

[51] Int. Cl.³ .............................................. G01B 3/10
[52] U.S. Cl. .................................... 33/179; 33/137 R
[58] Field of Search ............ 33/137, 138, 139, 178 R, 33/177, 179, 15, 16, 2

[56] References Cited

U.S. PATENT DOCUMENTS

| 458,564 | 9/1891 | Engel | 33/179 |
|---|---|---|---|
| 766,911 | 8/1904 | Stemm | 33/179 |
| 846,461 | 3/1907 | Engel | 33/137 X |
| 1,238,841 | 9/1917 | Snider | 33/179 |
| 1,491,444 | 4/1924 | Trahms | 33/179 |

Primary Examiner—Harry N. Haroian
Attorney, Agent, or Firm—Wilson, Fraser, Barker & Clemens

[57] ABSTRACT

A measuring device for ascertaining the perimeter of a cross-section of a body comprising an integral tape and slide guide. Laterally extending tabs at one end of the tape are foldable over a portion of the tape bent back upon the tab bearing end to form the slide guide. An aperture in the tab bearing end cooperates with indicia on the tape to display the perimeter of the tape loop extending from the slide guide.

1 Claim, 4 Drawing Figures

MEASURING TAPE

BACKGROUND OF THE INVENTION

1. Field of the Invention

This invention relates to measuring devices which are arranged to measure the perimeter of a body section, particularly an animal body section as employed in the manufacture of fitted custom garments.

2. Description of the Prior Art

The accurate fitting of pressure garments formed of elastic fabric to the wearer for various forms of treatment wherein perimeter tension results in inwardly directed pressures requires precise measurement of the perimeter of the section of the body portion on which it is placed. Such garments are fashioned from measurements which are proportioned, according to the pressures desired and the elasticity of the fabric employed, from precise perimeter measurements. Typically, treatment to inhibit scarring of a hand suffering from burns involves the application of a glove of elastic material which is fitted to the fingers, palm and heel of the hand to impose pressure on the injured region.

Measuring tapes are known for ascertaining the circumference or perimeter of a section of a body. Wrigley, U.S. Pat. No. 129,639 of July 16, 1872, discloses a tape with a slide fitting for a portion thereof secured to one end as by rivets and calibrations on the tape body to indicate the quantity of liquid contents in a vessel which it embraces. Wrigley suggests employing a scale of volumetric dimensions for a tank of given height on one face of the tape and a scale on the opposite face for indicating the reduction in measured volume for the thickness of the wall of the vessel. Bresson, U.S. Pat. No. 2,262,664 of Nov. 11, 1941, shows a measuring tape having a slotted fitting riveted to its end and calibrated on one face in circumference dimensions and on the other face in diameter dimensions so that the indicia positioned at the slot indicate diameter and circumference when the free end of the tape is passed around a round object and trained through the slot on the zero end of the tape.

Measuring instruments for fitting garments employing tapes extending transverse to a longitudinally extending strip adapted to be placed along an animal body to establish stations along said body at which the perimeter thereof is to be ascertained are shown in Jobst, U.S. Pat. No. 2,691,221 of Oct. 12, 1954. An improvement on the Jobst structure employing adhesive to ascertain the position of a closed loop of tape embracing a body portion is shown in Tenteris, U.S. Pat. No. 3,327,394 of June 27, 1967. The Tenteris instrument establishes a permanent template of the measured body portion since it can be separated from the body by severing the closed loops, however, such techniques permit but a single utilization of the instrument.

It is an object of this invention to improve and simplify the use of measuring and fittng devices to enable an unskilled attendant or even the prospective wearer of the garment which is to be made on the basis of measurement data taken to accomplish measurements. Another object is to enable reuse of the measuring instrument.

SUMMARY OF THE INVENTION

The measuring instrument of this invention comprises a tape of a flexible and inelastic sheet material such as paper, which includes a first elongate portion of a given width and adapted to be placed around a body section, the perimeter of which is to be determined. The first portion is closed to a second portion integral therewith, and having a width greater than the first portion so that the first portion can overlie the second portion in a longitudinal region and one or more side regions of the second portion can be folded longitudinally along the side of the longitudinal region over that region and the first portion. Thus, a slide is formed for the first portion integral with the tape and out of the material of the second portion to secure a loop of the tape for convenient manipulation on the body section, the perimeter of which is to be measured. Indicia of longitudinal dimensions are formed on the first portion of the tape and so located as to indicate with respect to indexing means on the second portion of the tape, the length of the perimeter region defined by the slide; that is, the length of tape extending from the slide on the second portion of the tape to the point of return of the distal first portion of the tape into the slide. A feature of this structure is the use of an aperture in the second portion of the tape as a window providing the indexing means when indicia on the first portion of the tape are exposed in registry with the window. Anther feature involves slide defining tabs on opposite sides of the longitudinal region of the second portion to embrace the returned first portion for reciprocal motion within the slide while the tab overlying relationship is maintained by light finger pressure.

The above and other features of this invention will be appreciated more fully from the following detailed description when read with reference to the accompanying drawing in which:

DESCRIPTION OF THE PREFERRED EMBODIMENT

Figure 1:
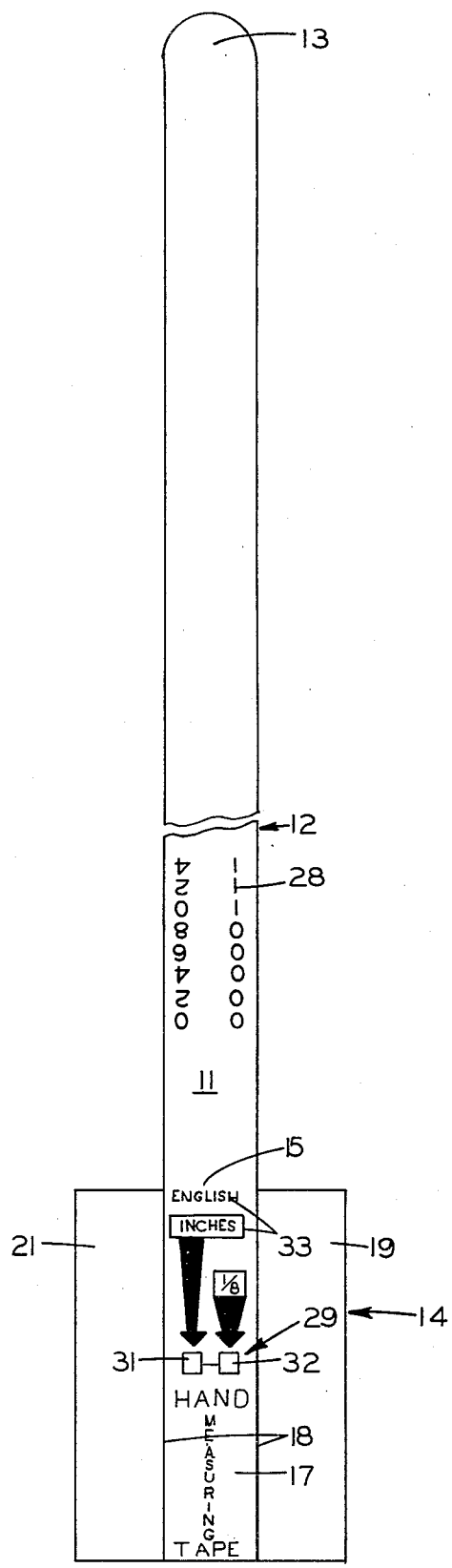
FIG. 1 is a plan view of one face of a measuring tape embodying features of this invention.

A measuring tape illustrative of this invention is shown in the drawings to comprise a strip of flexible inelastic sheet material 11 having a first elongate portion 12 having a given maximum width W which may be uniform throughout its length. Portion 12 extends from a free end 13 a distance greater than the perimeter length to be measured by the tape to a second portion 14 integral therewith and extending longitudinally from end 15 of portion 12. Second portion 14 has a transverse dimension SW greater than the given maximum width W of portion 12.

Figure 2:
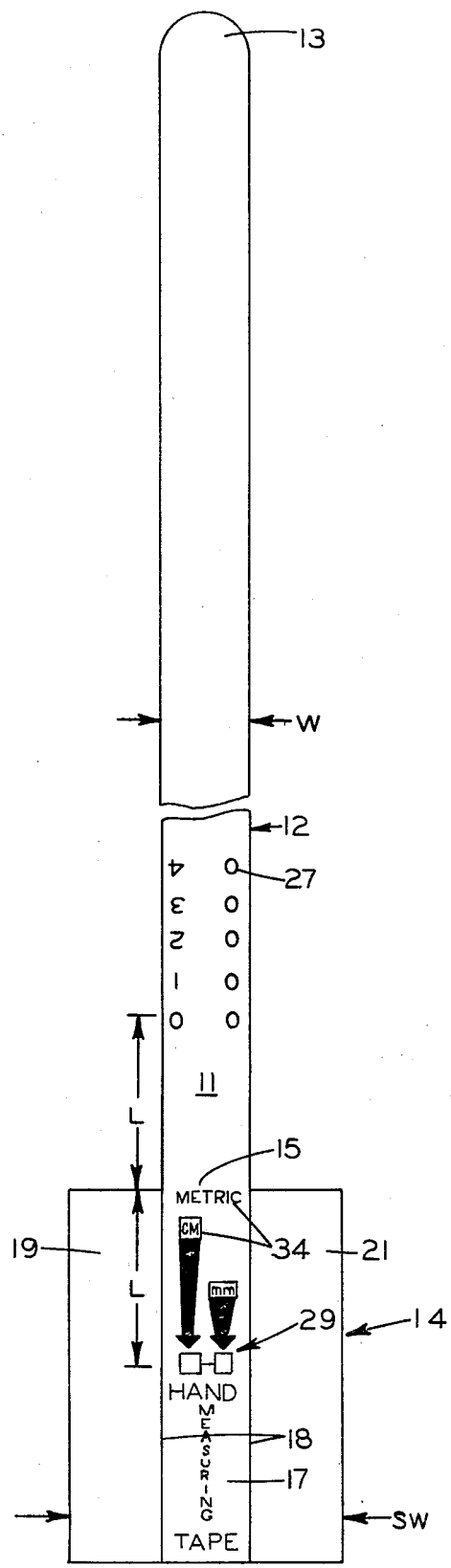
FIG. 2 is a plan view of the measuring tape of FIG. 1 showing the face opposite that shown in FIG. 1.
Figure 3:
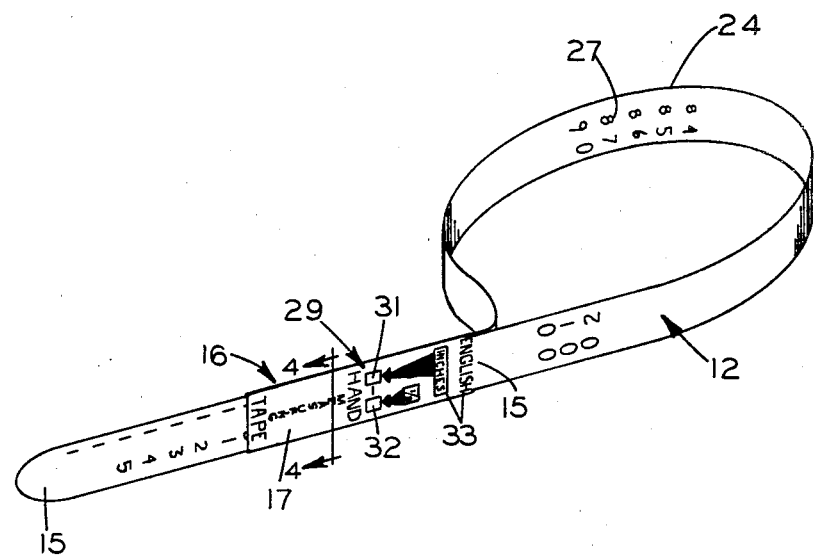
FIG. 3 is a perspective view of the measuring tape of FIGS. 1 and 2 arranged for measurment of body section perimeters.
Figure 4:
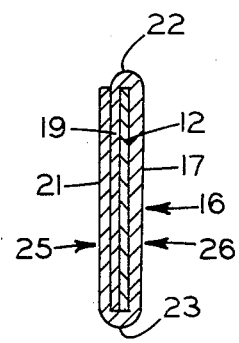
FIG. 4 is an enlarged cross-section of the slide region of FIG. 3 taken along the line 4—4 of FIG. 3.

The second tape portion 14 is adapted to be formed into a slide 16 to embrace and guide the first portion 12 for relative longitudinal reciprocation therein when the first portion end 13 is turned back upon portion 12 at end 15. Advantageously, the second portion 14 is made up of a central longitudinal region 17 having a width slightly in excess of width W of portion 12 defined by longitudinal margins 18 aligned with the extension of the longitudinal axis of portion 12 which forms the longitudinal axis of second portion 14 and central region 17. A side region 19, or a pair of opposed side regions 19 and 21, of a transverse dimension approximately that of width W extends as a tab from a margin 18 of central region 17 or, as the case may be, as tabs from margins of the region. These tabs 19 and 21 are arranged to be folded over the central region 17 along margins 18 to form an open ended pocket or slide 16 for the reception of first portion 12 as shown in FIGS. 3 and 4. The fold line can be located accurately by scoring the sheet stock from which portions 12 and 14 are formed along the margins 18 as shown in cross-section at the scores 22 and 23 of FIG. 4. The total width of portion 14 having opposed tabs 19 and 21 is typically about three times the width W, as shown at SW in FIG. 2.

Measurements are accomplished by determining the length of portion 12 from its end 15 contiguous to the integral slide 16 to the entry of the distal end of portion 12 into the slide. In assembling the tape for measurment of a perimeter, portion 12 is turned back upon itself and its distal end laid against the central region 17 of second portion 14 to form a loop 24 as shown in FIG. 3. Tabs 19 and 21 are then folded along margins 18 over the length of portions 12 superimposed on region 17 to form slide 16 which may be maintained by finger pressure on the faces 25 and 26 of FIG. 4. The loop 24 is adjusted in size by reciprocation of portion 12 in slide 16. The loop is formed large enough to be positioned over the body section to be measured (not shown) and then drawn down snugly on the body section to establish the length of the perimeter of that section.

Loop length and body section perimeter are indicated by indicia 27 and 28 of longitudinal dimensions positioned along the length of first portion 12 which cooperate with indexing means 29 on second portion 14 to indicate length by alignment of indicia with the indexing means.

The illustrative tape is calibrated in English units of length as indicia 27 on one face, and in Metric units of length as indicia 28 on the opposite face. Indexing means 29 are shown in the form of apertures 31 and 32 in the central region 17 of second portion 14 forming windows through which registering indicia 27 or 28 may be viewed. Two windows 31 and 32 are shown with the indicia of inches and eighths of inches respectively displayed when one face of central region 17 forms an outer face of slide 16 by the folding of tabs 19 and 21 away from that face. When metric measurements are to be made, the tabs 19 and 21 are folded away from the opposite face of central region 17. Suitable legends 33 and 34 are arranged on the central region 17 to identify the units of measurement. It will be noted that the legends of a system are on the face of region 17 which is opposite that contiguous with the face of portion 12 bearing the indicia of length so that the indicia of length are on the inner face of the measurement loop 24.

Placement of the zero length indicia on portion 12 is determined by the placement of the index means on region 17. In the case of windows 31 and 32 located at distance L from the tape receiving end of the slide contiguous with end 15, the indicia are spaced along portion 12 a distance L from end 15. The scale of indicia are placed at appropriate length increments fro the zero length reference positions in increasing graduations toward the distal end 13 of portion 12.

A tape with slide as described, can be formed by inexpensive printing and die cutting techniques. When made of paper, it is a relatively inexpensive instrument of measurement which can be disposed of after use which such action is dictated, as by health care considerations. However, it is sufficiently rugged and convenient for manipulation to be utilized repetatively. Measurements can be made in either system provided on the tape from a single instrument by reversal of the tabs. It is contemplated that tabs 19 and 21 can be secured together as by adhesive to maintain the slide structure although such securing has not been found necessary in practice under normal circumstances.

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed is:

1. A measuring device comprising a strip of flexible non-elastic sheet material having a given maximum width along a first portion thereof extending from one free end to a second end attached to one end of a second portion of said strip, said second portion including an opposite free end and having a central longitudinal region and two adjacent side regions, said second portion having a second width greater than said given maximum width such that said side regions are foldable longitudinally of said strip so as to cover said central longitudinal region on one face thereof and to form a slide to receive said first portion of said strip of said given maximum width, said first portion being calibrated on said one face in indicia of longitudinal dimensions, said second portion having aperture means formed in said central longitudinal region and indexing means on an opposite face of said central longitudinal region for cooperating with said indicia of longitudinal dimensions to define said indicia characterizing the length of said strip extending from said slide toward said one free end and returned to said slide adjacent said second end of said first portion.

* * * * *